United States Patent [19]

Kawaguchi et al.

[11] Patent Number: 5,250,265
[45] Date of Patent: Oct. 5, 1993

[54] AUTOMOTIVE SOLAR-OPERATED DEODORIZER WITH SOLAR CELL COOLING AND AUTOMATED OPERATIONAL CONTROL

[75] Inventors: Kiyoshi Kawaguchi, Toyota; Norihisa Itoh, Anjo; Kouji Yamashita, Tokaishi; Kazuma Matsui, Toyohashi, all of Japan

[73] Assignee: Nippondenso Co., Ltd., Kariya, Japan

[21] Appl. No.: 879,549

[22] Filed: May 4, 1992

Related U.S. Application Data

[63] Continuation of Ser. No. 682,410, Apr. 8, 1991, abandoned, which is a continuation of Ser. No. 401,410, Sep. 1, 1989, abandoned.

[30] Foreign Application Priority Data

Sep. 5, 1988 [JP] Japan ............................ 63-222045
Aug. 5, 1989 [JP] Japan ............................ 1-203640

[51] Int. Cl.⁵ .............................................. A61L 9/12
[52] U.S. Cl. .................................... 422/107; 422/124; 422/306; 422/5; 239/57; 239/60; 239/73
[58] Field of Search ............ 422/4, 5, 120, 121, 422/123, 124, 306, 107; 136/291; 239/57, 58, 59, 60, 71, 73

[56] References Cited

U.S. PATENT DOCUMENTS

| | | | |
|---|---|---|---|
| 3,576,593 | 4/1971 | Cicerello | 422/4 |
| 4,095,997 | 6/1978 | Griffiths | 126/432 |
| 4,339,079 | 7/1982 | Sato et al. | 239/57 X |
| 4,372,490 | 2/1983 | Le Caire, Jr. et al. | 239/59 |
| 4,558,634 | 12/1985 | Oshiro et al. | 98/2.18 |
| 4,568,521 | 2/1986 | Spector | 422/124 |
| 4,666,638 | 5/1987 | Baker et al. | 239/57 X |
| 4,840,770 | 6/1989 | Walz et al. | 239/60 X |

FOREIGN PATENT DOCUMENTS 59-32508 2/1984 Japan.
1-11241 3/1989 Japan.

OTHER PUBLICATIONS

Perry, R. H. et al., "Perry's Chemical Engineer's Handbook," 6th ed., N.Y., McGraw-Hill, 1984, pp. 6.21–6.22.

Primary Examiner—James C. Housel
Assistant Examiner—Jeffrey R. Snay
Attorney, Agent, or Firm—Cushman, Darby & Cushman

[57] ABSTRACT

A deodorizer which comprises a deodorant member, an electric motor, a fan fixed to the electric motor, a receptacle having these members accommodated therein, and a solar cell provided in the receptacle and adapted to supply a driving electric power to the electric motor, whereby, owing to the blowing action of the fan, air is caused to enter the interior the receptacle from an air suction port and pass therethrough and is blown out from an air blowout port to outside the receptacle, and the air is caused to flow around a portion of the receptacle where the solar cell is installed.

19 Claims, 18 Drawing Sheets

AUTOMOTIVE SOLAR-OPERATED DEODORIZER WITH SOLAR CELL COOLING AND AUTOMATED OPERATIONAL CONTROL

This is a continuation of application Ser. No. 07/682,410, filed on Apr. 8, 1991, which was abandoned upon the filing hereof, and which is a file wrapper continuation of application Ser. No. 07/401,410 filed Sep. 1, 1989, also abandoned.

BACKGROUND OF THE INVENTION

The present invention relates to a deodorizer which is driven to operate by means of a solar cell.

Conventionally, in this type of deodorizer, as disclosed in, for example, Japanese Utility Model Unexamined Publication No. 59-32508, an electric motor is driven to rotate by the action of a solar cell. The open air is introduced into a receptacle by operation of a fan fixed to the electric motor. Thus, the smelly components in the air are deodorized by a deodorant member installed within the receptacle, the resulting air being blown outside the receptacle.

The above-described known deodorizer indeed has an advantage in that, for example, there is no need to conduct replacement of any battery because of the use of a solar cell, but, on the other hand, has a disadvantage in that it is necessary to install such a solar cell in a place exposed to sunrays, which is followed by a high likelihood that the temperature of the solar cell will become high.

This leads to heat deterioration of the solar cell, which leads to a shortening of the service life of the solar cell.

SUMMARY OF THE INVENTION

The present invention has been made in view of the problems of the above-described prior art and an object thereof is to provide a deodorizer which is capable or reducing the degree of heat deterioration of a solar cell.

According to the present invention, there is provided a deodorizer which comprises an electric motor, a fan fixed to the electric motor, a receptacle accommodating therein the electric motor and fan, and a solar cell provided on the receptacle and used to supply a driving electric power to the motor, whereby an open air is passed through the interior of the receptacle and is blown outside the same owing to the blowing action of the fan and, at this time, the stream of air in the receptacle is caused to flow around a portion of the receptacle where the solar cell is located.

In the present invention, the receptacle may be constituted by a casing the top of which is opened and the longitudinal section of which is in the form of a recess, and a cover which is openably provided over the casing. In this case, the solar cell may be provided on an outer surface of the cover of the receptacle.

In the present invention, the inside surface of the cover corresponding to the outside surface thereof where the solar cell is provided may be kept in opposing or corresponding relation to an air blow passage including an air suction port, a deodorant member, the fan, and an air blowout port.

In the present invention, the receptacle may be provided with an observation port for observing the rotation of the fan.

In the present invention, the deodorant member may be arranged such that it is removably installed within the receptacle.

Further, in the present invention, the solar cell may be mounted within the receptacle.

In the present invention, the electric motor is driven to rotate by operation of the solar cell and the fan is caused to rotate. As a result, the air is passed through the interior of the receptacle and then is blown outside the receptacle by the blowing action of the fan. Accordingly, when the air is caused to pass through the interior of the receptacle, the smell or odor is deodorized by a deodorant member within the receptacle.

On the other hand, owing to heat transfer by forced convection effected due to passage of the air through or around the portion of the solar cell, the heat of the solar cell continues to be taken away. This makes it possible to reduce the temperature of the solar cell.

According to the present invention, not only the deodorizing effect but also the heat deterioration reducing effect with respect to the solar cell can be obtained. Therefore, it is possible to maintain the deodorizing effect for a long period of time. Thus, the effect of the invention as viewed from the practical point of view is great.

In addition, the cooling construction per se for solar cell concurrently utilizes the fan for deodorization and therefore is simplified, thus providing an effect that such simplification can contribute to miniaturization of the deodorizer.

DESCRIPTION OF THE PREFERRED EMBODIMENTS

Figure 1:
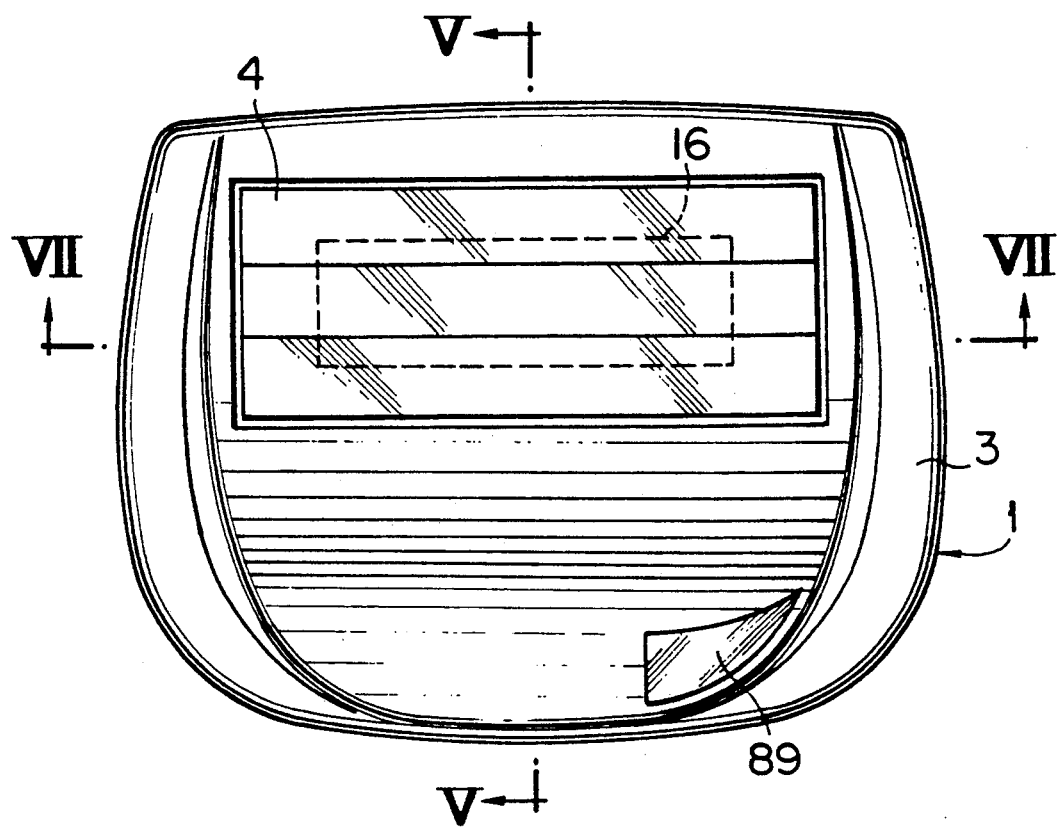
FIG. 1 is a plan view showing a deodorizer in accordance with a first embodiment of the present invention.

Referring now to FIGS. 1 to 8, a deodorizer has a main part which is composed of a receptacle 1, a solar cell 4, a deodorant member 5, an electric motor 7, and a fan 9. As will be understood from the Figures, the receptacle 1 is composed of a casing 2 and a cover 3, the casing 2 has its top surface opened and is shaped like a recess in vertical section, and the cover 3 is provided on the opening of the casing 2 in such a manner that the cover can be opened and closed via hinges 10 with respect to the same.

The casing 2 of the receptacle 1 is made of a heat-resisting ABS resin while the cover 3 is made of heat-resisting acrylic resin. The casing 2 is substantially square in cross section and is substantially planar in vertical section. On the other hand, the cover 3 is made substantially square in cross section and is shaped to be arcuate and slant in vertical section.

The solar cell 4 is of an amorphous silicon type.

Figure 34:
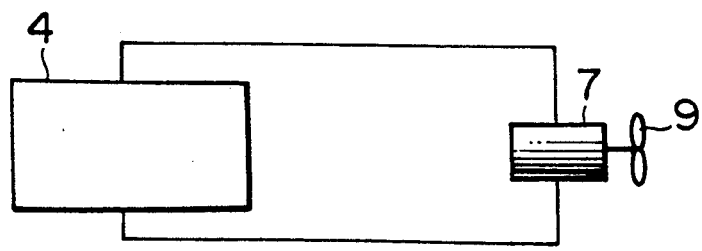
FIG. 34 is an electric circuit diagram showing the solar cell and an electric motor, both being employed in the deodorizer in accordance with the first embodiment of the present invention.

The deodorant member 5, electric motor 7, and the fan fixed to the electric motor 7 are accommodated within the casing 2 of the receptacle 1. The electric motor 7 has terminals 13 (see FIG. 28) to which output leads 6 of the solar cell 4 are directly connected without providing any switch. For this reason, the electric motor 7 is directly driven to rotate by the generated output of the solar cell 4. An electric circuit diagram of this embodiment is shown in FIG. 34.

A slit-shaped air suction port 17 and a slit-shaped air blowout port 18 are provided in opposite short side portions of the receptacle 1.

The air, owing to the blowing action of the fan 9, is allowed to enter the interior of the receptacle 1 via the air suction port 17 and then is allowed to pass through the interior of the receptacle and then is allowed to blow outside the receptacle 1 via the air blowout port 18. At this time, the air which passes through the receptacle 1 is so arranged as to flow around the other side surface of the cover portion than that side surface, on which the solar cell 4 is installed.

Figure 3:
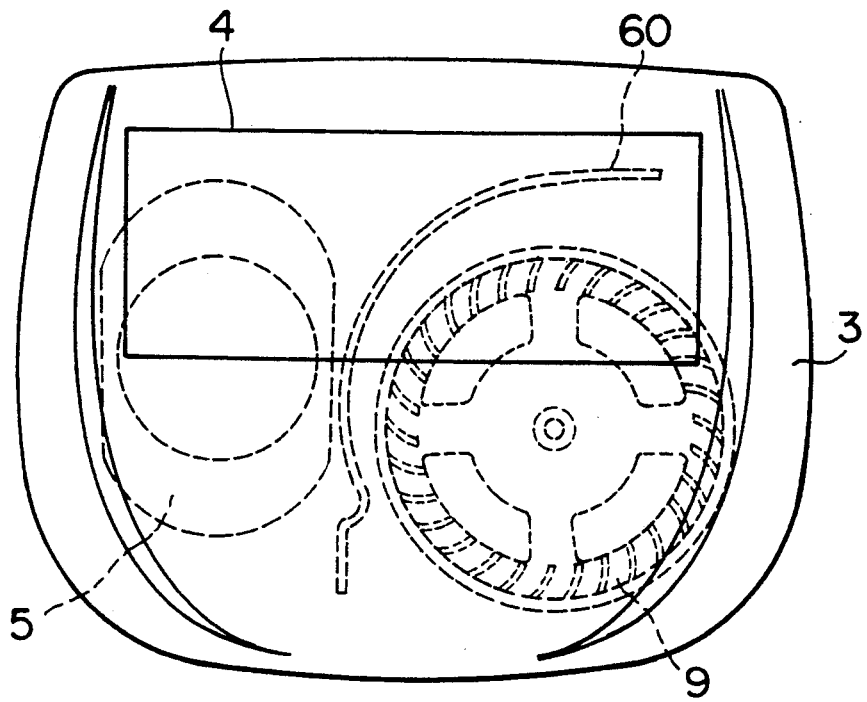
FIG. 3 is a plan view schematically showing an internal construction of the deodorizer of FIG. 1.
Figure 4:
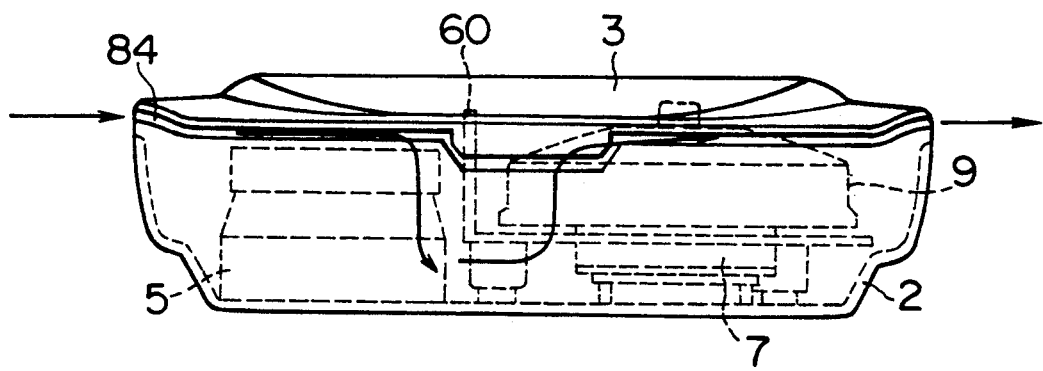
FIG. 4 is a front view schematically showing an internal construction of the deodorizer of FIG. 2.
Figure 5:
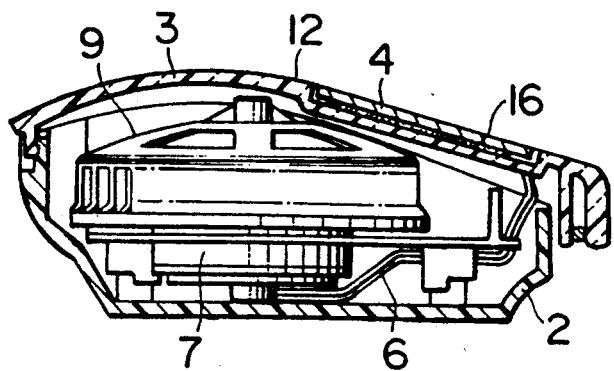
FIG. 5 is a sectional view taken along the line V—V of FIG. 1.
Figure 7:
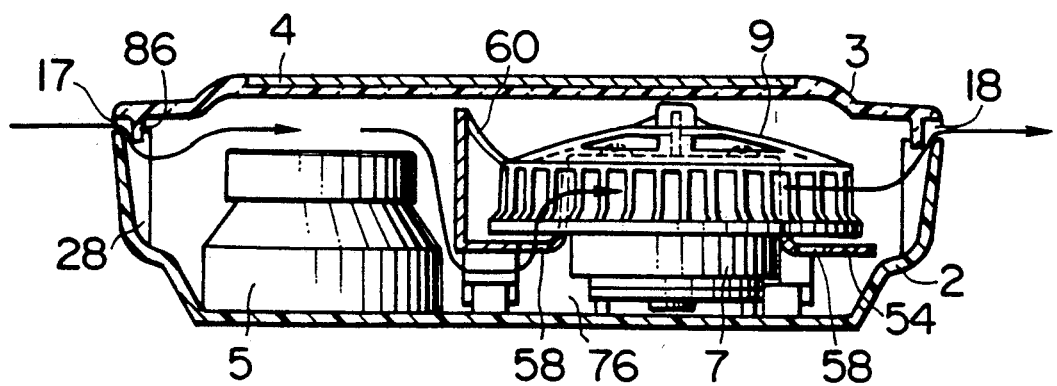
FIG. 7 is a sectional view taken along the line VII—VII of FIG. 1.

Namely, as will be understood from FIGS. 3 and 7, the solar cell 4 is installed so that the solar cell 4 covers the deodorant member 5 and the fan 9 in the projecting direction of the slant surface of the receptacle 1 and so that the solar cell 4 overlaps an imaginary plane connecting the air suction port 17 and the air blowout port 18. As a result, the other side surface of the receptacle 1 than that side surface, on which the solar cell 4 is mounted faces over the blown air passage system including the air suction port 17, deodorant member 5, fan 9 and air blowout port 18. Accordingly, the air which passes through the interior of the receptacle 1 owing to the blowing action of the fan 9 is allowed to flow along the other side surface of the cover portion than that side surface, on which the solar cell is mounted.

The foregoing description refers to the construction of the main part of the deodorizer. Next, reference will be made to a detailed construction of the deodorizer.

Figure 8:
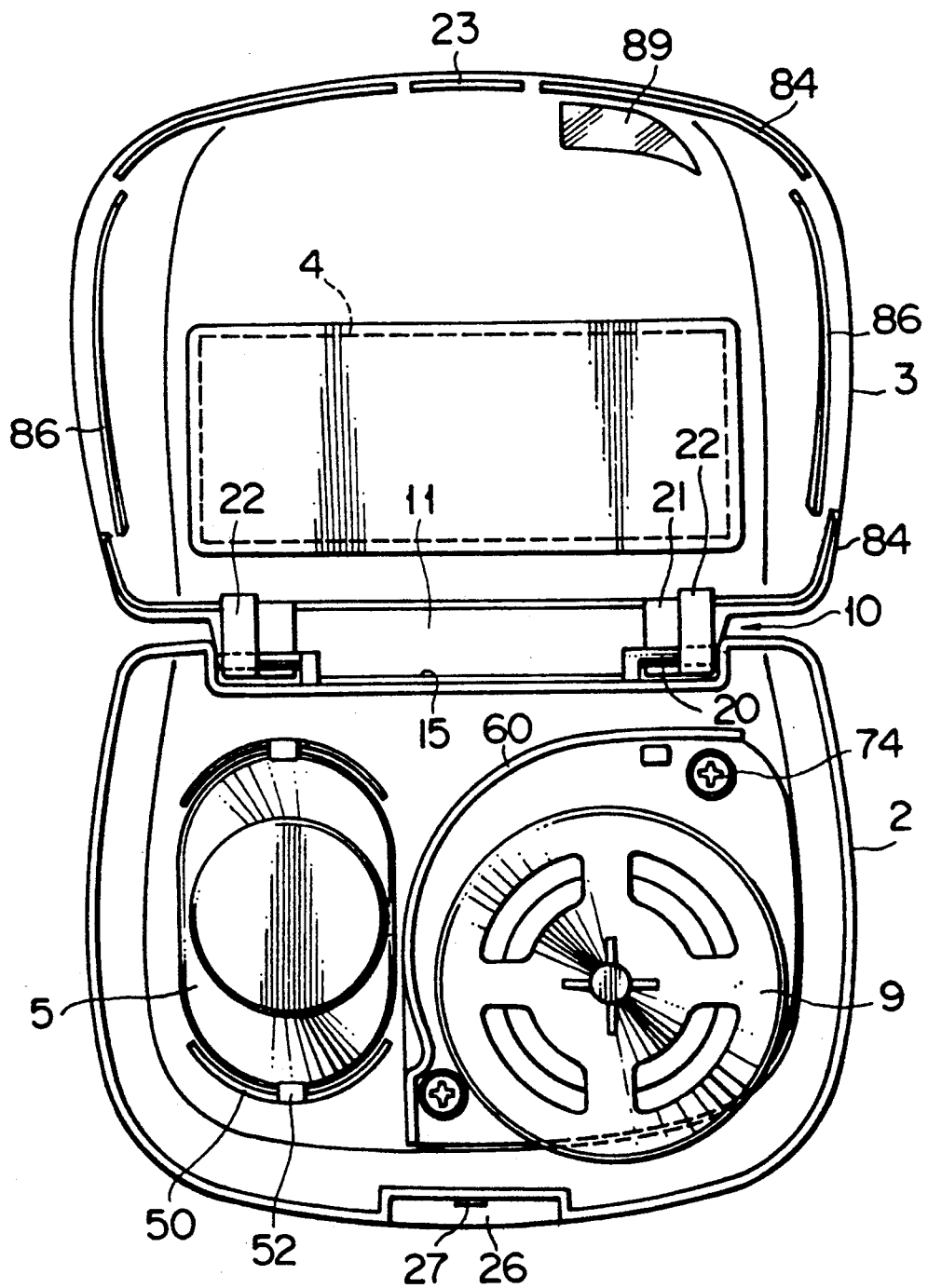
FIG. 8 is a plan view showing a state wherein the cover shown in FIG. 1 is opened.
Figure 9:
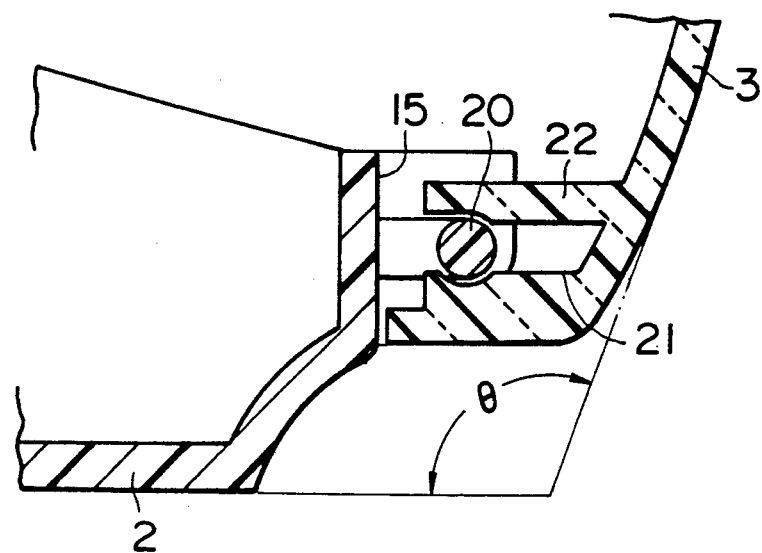
FIG. 9 is a sectional view showing a hinge construction between a casing and the cover shown in FIG. 8.

The casing 2 and the cover 3 are connected to each other by means of a hinge mechanism 10 as stated above, the hinge mechanism having the following construction. Referring to FIGS. 8 and 9, one of two opposite sides of the casing 2 is formed with a recess 15 and a pair of L-shaped pins 20 are integrally formed on two opposite end portions of this recess 15, respectively. On the other hand, the cover 3 is formed integral with a protrusion 11 at a position thereof which corresponds to the recess 15. Holding portions 21, 22 which define a gap therebetween, the gap having a size slightly smaller than the diameter of the pin 20, are integrally formed on the protrusion 11 at the positions corresponding to the paired L-shaped pins 20 thereof, respectively.

The holding portions 21, 22 of the cover 3 are applied to a straight portion of each pin 30 of the casing 2 and are pressed onto the same. The gap between the holding portions 21 and 22 are thereby widened by the straight portion, so that the holding portions 21, 22 are brought into elastic contact with the straight portion of each pin 20. As shown in FIG. 9, since the portions of the holding portions 21, 22 where the same are allowed to contact with the straight portion are shaped into circular arcs, the opposing surfaces of the paired holding portions 21, 22 are allowed to contact with the straight portion of each pin 30 in good condition, thus providing a good level of interfitting between each two surfaces.

Consequently, the casing 2 and the cover 3 are attached to each other in such a manner that the cover 3 can be opened and closed with respect to the casing 2. It is to be noted that, as shown in FIG. 9, the degree of opening $\theta$ of the cover 3 reaches a value of about 130°, the holding portion 21 of the cover 3 has its fore end allowed to contact with a bottom portion of the recess 15 of the casing 2. When the cover 3 is opened through the degree of opening $\theta$ or more, the protrusion 11 of the cover 3 or the fore ends of the holding portions 21 work as fulcrums so as to permit the holding portions 21, 22 of the cover 3 to be disengaged from the straight portions of the pins 20 of the casing 2 due to the principle of the lever.

Figure 10:
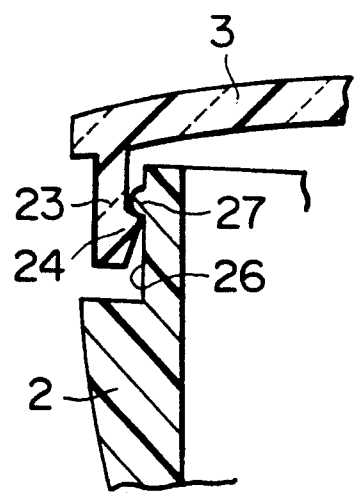
FIG. 10 is a sectional view showing a locking mechanism for locking the cover to the casing shown in FIG. 8.

In order to maintain the opening 8 of the casing 2 in a closed condition by use of the cover 3, a locking mechanism for locking the cover 3 to the casing 2 is provided. As shown in FIG. 10, on a portion of the cover 3 opposite to the portion thereof where the holding portions 21, 22 are provided, a projection 23 is integrally formed and, a latch portion 24 is integrally formed on the projection 23. On the other hand, on a portion of the casing 2 corresponding to the projection 23, a recessed portion 26 is integrally formed in such a manner that the recessed portion 26 is allowed to project inside the casing 2. In addition, on a surface of the recessed portion 26 is formed a projection 27 whose outer surface is semicircular in section. For this reason, when the cover 3 has been closed, the latch portion 24 of the cover 3 rides over the projection 27 of the casing 2, whereby the latch portion 24 comes into engagement with the projection 27. When it is desired to disengage, a finger is used to press the recessed portion 26 of the casing 2 and thereby elastically deform the recessed portion. In this state, the cover 3 is lifted up.

Figure 6:
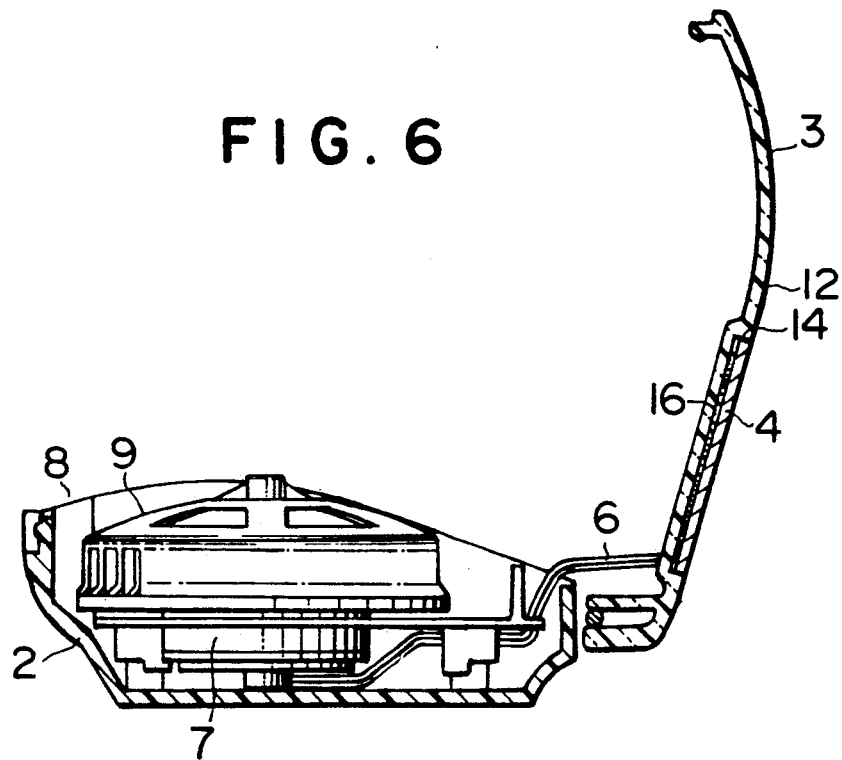
FIG. 6 is a sectional view showing a state wherein a cover in the sectional view of FIG. 5 is opened.
Figure 11:
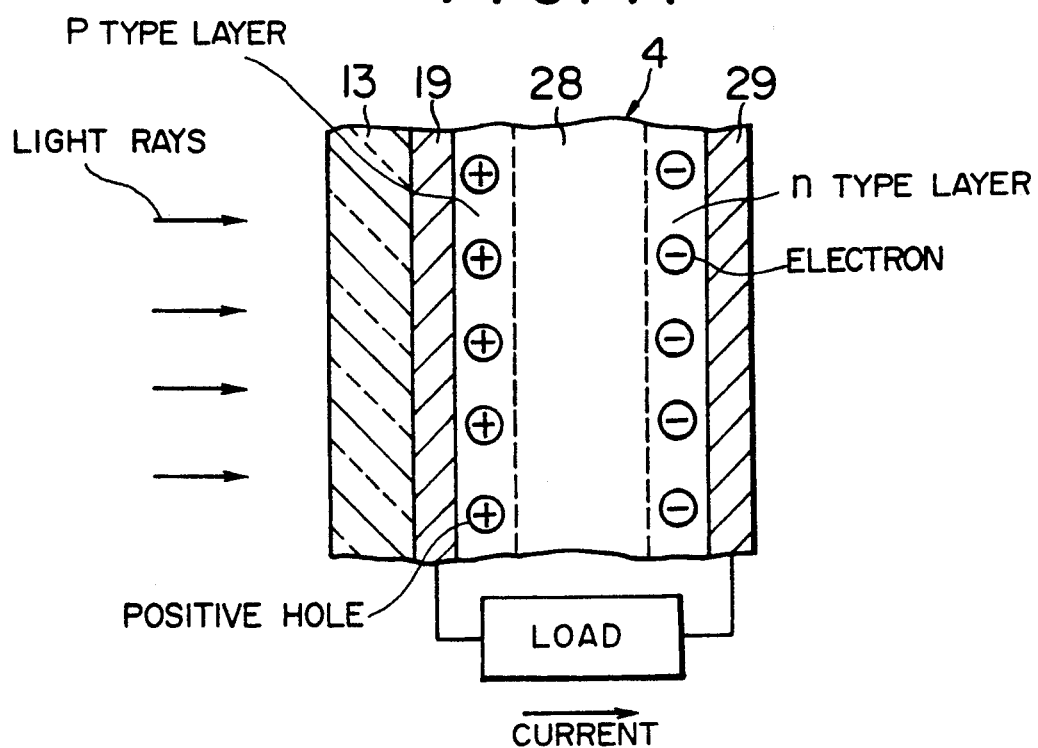
FIG. 11 is a schematic sectional view showing the internal construction of a solar cell employed in the deodorizer in accordance with the first embodiment of the present invention.

The solar cell 4 has a construction shown in FIG. 11. Namely, the solar cell 4 is composed of a glass substrate 13, a transparent electrode 19, a metal electrode 29, and a pn junction type or pin type amorphous silicon layer 28. On the surface of the glass substrate 13 is formed an anti-reflection coating or a useless ray wavelength band elimination filter (not shown). On the surface of the amorphous silicon layer 28 are bonded the transparent electrode 19 and metal electrode 29 and, on the surface of that transparent electrode 19, the glass substrate 13 is bonded. As shown in FIG. 6, the solar cell 4 is adhered in a depression 14 of a slant surface 12 of the cover 3 with the metal electrode 29 facing the bottom of the depression 14, via a so-called duplicated tape 16 having an elastic base plate provided, on both surfaces thereof, with adhesive layers respectively.

Figure 13:
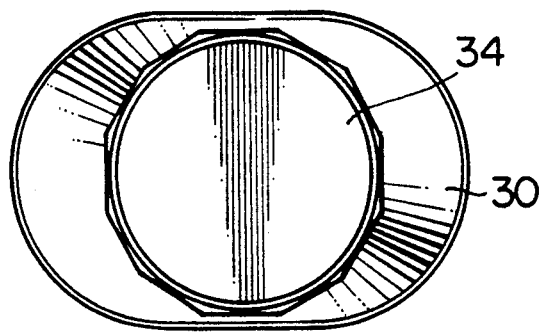
FIG. 13 is a plan view showing a deodorant member employed in the deodorizer in accordance with the first embodiment of the present invention.
Figure 14:
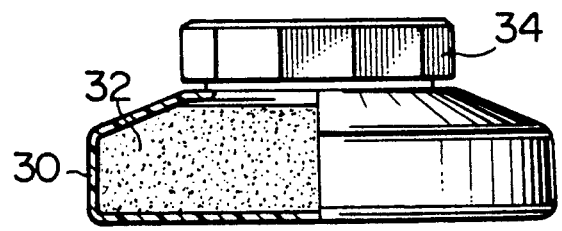
FIG. 14 is a partly sectional view of the deodorant member of FIG. 13.

As shown in FIGS. 13 and 14, the deodorant member 5 is composed of a container made of resin such as polypropylene, deodorant 32 filled in the container 30, and a cap 34 made of resin such as polypropylene and intended to open and close an opening of the container 30. The container 30 is constructed such that the bottom surface configuration thereof is in the form of an ellipse. The container 30 rises from its bottom surface in the upward direction while maintaining its configuration to be in the form of an ellipse (the cross-sectional area is constant). Thereafter, the container 30 is upwardly tapered, i.e., the cross-sectional area thereof is gradually reduced toward the top of the container. Finally, the top portion thereof is shaped like a hollow cylinder 40 whose diameter is constant.

The cap 34 is rotatably fitted over the hollow cylinder 40 of the container 30 and has the following construction. As shown in FIGS. 15 to 21, on the side surface of the hollow-cylinder 40 of the container 30, a pair of threads 42 are formed at two opposite regions, respectively, each region extending through 90° as measured about a center of the hollow-cylinder 40. On the other hand, on the inner side surface of the cap 34, a pair of threads 44 are also formed at two opposite regions, respectively, each region extending through 90° as measured about a center of the cap 34.

Figure 15:
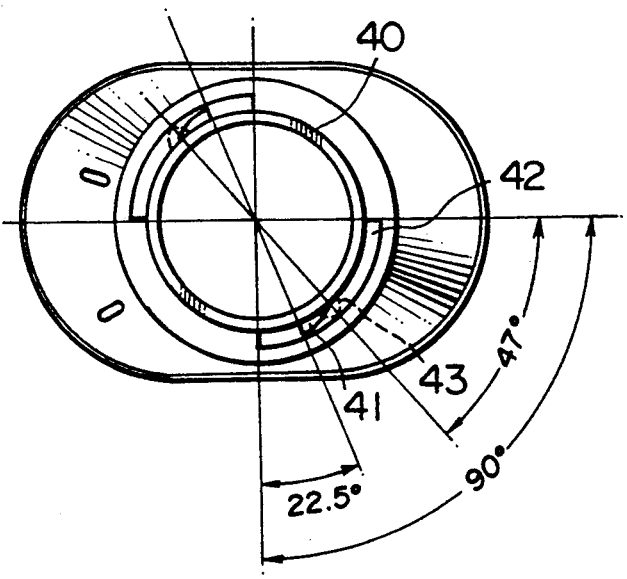
FIG. 15 is a plan view showing a container portion of the deodorant member of FIG. 13 from which a cap is taken away.
Figure 16:
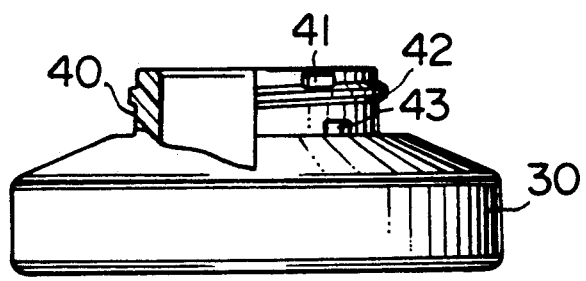
FIG. 16 is a partly sectional view of the deodorant member of FIG. 15.

As shown in FIG. 15, upper surfaces of the two threads 42 of the hollow cylinder 40 of the container 30 are formed thereon with uncork positioning ribs 41 for the cap 34 at positions of 22.5° as measured from the fore ends of the threads 42. Further, the hollow cylinder 40 is formed, below the threads 42, with detent ribs 43 at positions of 47° as measured from the fore ends of the threads 42.

Figure 17:
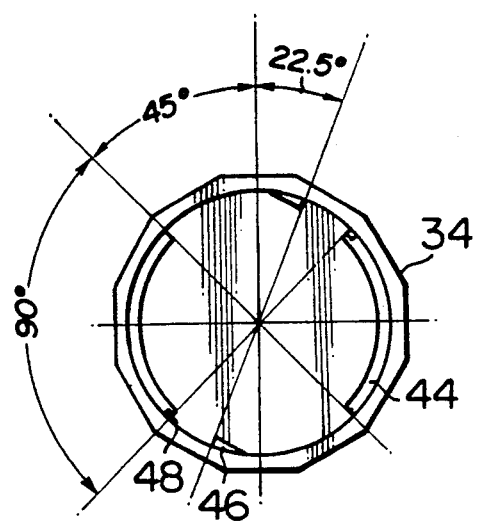
FIG. 17 is a bottom view showing a rear face side of the cap on the deodorant member of FIG. 13.
Figure 18:
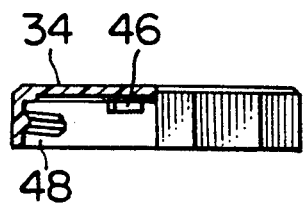
FIG. 18 is a partly sectional view of the cap of FIG. 17.
Figure 19:
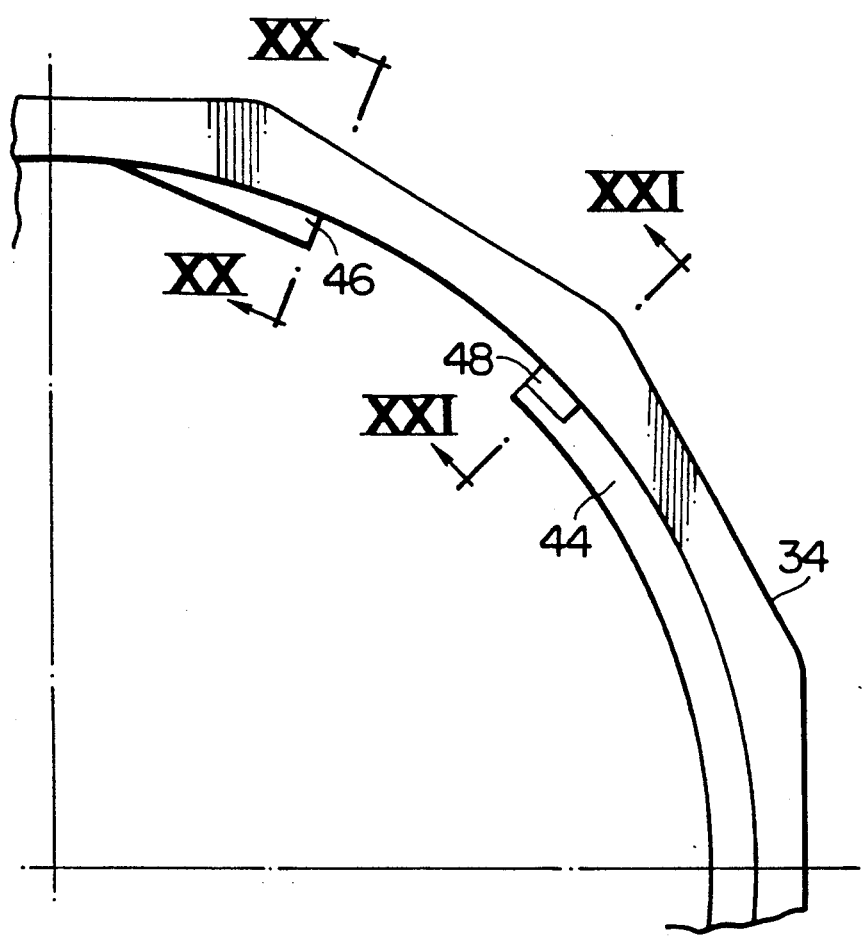
FIG. 19 is a bottom view, partly enlarged, of the cap of FIG. 17.
Figure 20:
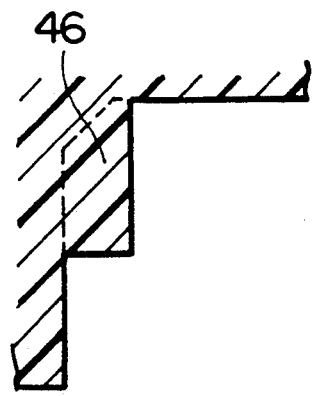
FIG. 20 is a sectional view taken along the line XX—XX in FIG. 19.
Figure 21:
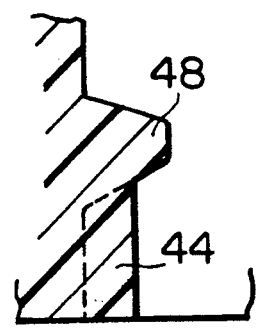
FIG. 21 is a sectional view taken along the line XXI—XXI in FIG. 19.

As shown in FIG. 17, the inner side surface of the cap 34 is formed, at two opposite portions, with two uncork positioning ribs 46 at positions of 22.5° as measured from a center line of the cap 34. Further, detent ribs 48 are formed on the surfaces of the fore end portions of the two threads 44 of the cap 34, respectively.

With the above-described construction of the hollow cylinder 40 of the container 30 and the cap 34, when the cap 34 is gradually turned, the detent ribs 48 thereof abut against the detent ribs 43 of the hollow cylinder 40 of the container 30. However, each of the detent ribs 43, 48 is formed such that the outer surface thereof is smooth and tapered and is shaped to have a chevron-shape in section. Therefore, if the cap 34 is turned with application thereto of a slightly large force, the detent rib 48 can ride over the detent rib 43 of the container 30.

After the detent rib 48 rides over the detent rib 43 in this way, the cap 34 is located between the detent rib 43 of the container 30 and the uncork positioning rib 41 thereof. When the cap 34 is further turned from this location, one of the uncork positioning ribs 46 of the cap 34 abuts against the uncork positioning rib 41 of the container 30, whereby the position of the cap 34 is fixed.

The deodorant 32 is in the form of a gel. The deodorant components are aromatic and are of an evapotranspiration type and are filled in the container 30.

Figure 25:
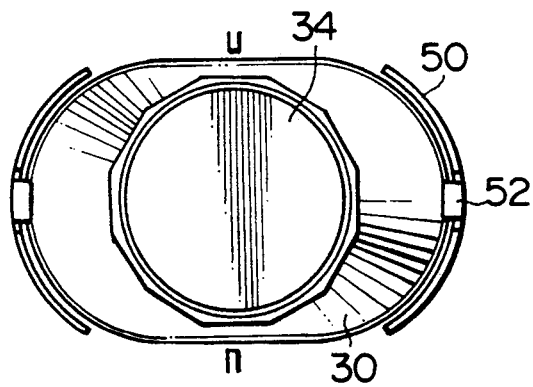
FIG. 25 is a plan view showing a fixing construction for fixing the deodorant member.
Figure 26:
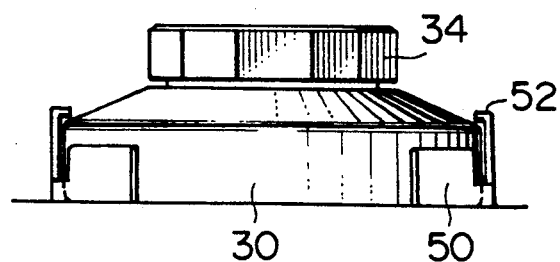
FIG. 26 is a front view of the construction of FIG. 25.

The deodorant member 5 having the described construction is installed within the casing 2 of the receptacle 1 of the deodorizer, the construction for installation being made as follows. As shown in FIGS. 25 and 26, the bottom of the casing 2 is integrally formed, at two opposite positions, with two arcuate protrusions 50, respectively, which are adapted to hold the side surfaces of the container 30 of the deodorant member 5. In addition, a pair of projection-like latch portions 52 are integrally formed on the paired protrusions at intermediate portions thereof, respectively. With this construction, one side surface of the container 30 of the deodorant member 5 is inclned and then is brought into engagement with one latch portion 52 and projection 50. Thereafter, the other side surface of the container 30 is applied under pressure onto the other latch portion 52 and is pushed toward the bottom of the casing 2. Thus, the container 30 is reliably held by the elastic reaction force of the projection-like latch portions.

Figure 27:
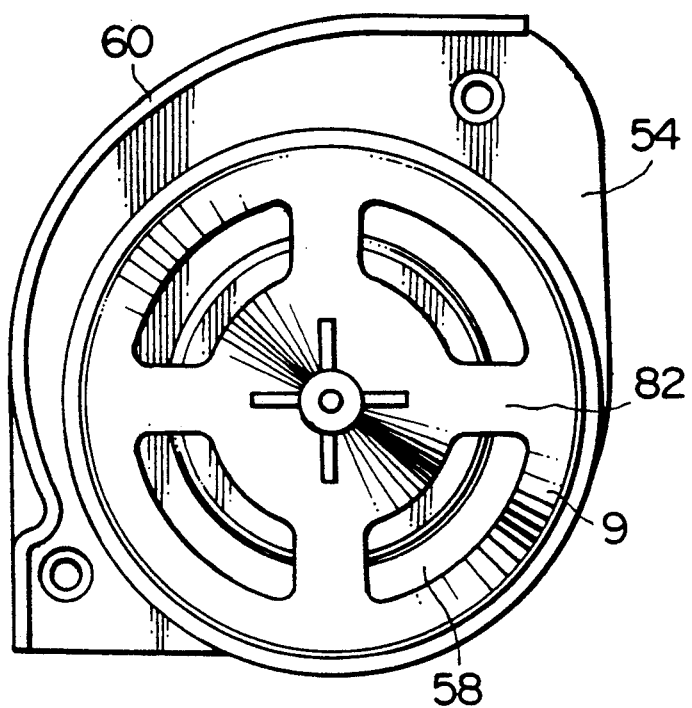
FIG. 27 is a plan view showing the construction of a fan section, that fan of which is employed in the deodorizer in accordance with the first embodiment of the present invention.
Figure 28:
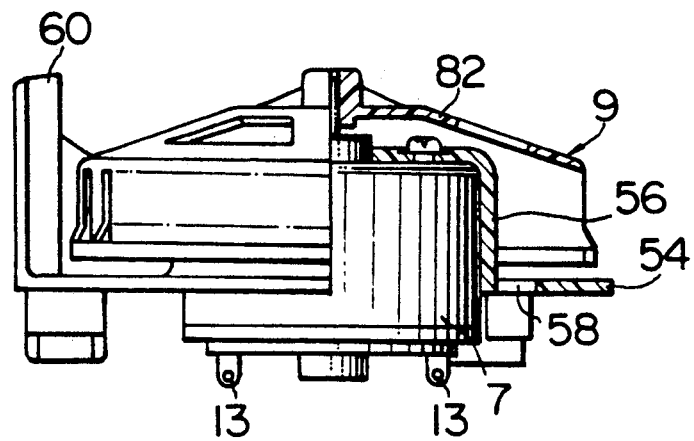
FIG. 28 is a partly sectional view of the construction of FIG. 27.

As shown in FIGS. 27 and 28, the electric motor 7 is disposed inside a central cylindrical portion 56, serving as a motor stay, of a resinous mounting base plate 54. The motor thus is fixed to the mounting base plate 54 by means of screws. The mounting base plate 54 is formed with four air introduction portions 58 in the vicinity of the bottom portion of the central cylindrical portion 56.

The mounting base plate 54 is formed integral with a scroll section 60 having a smooth curved surface so as to permit the air to flow toward the air blowout port 18 of the receptacle 1 of the deodorizer.

Figure 31:
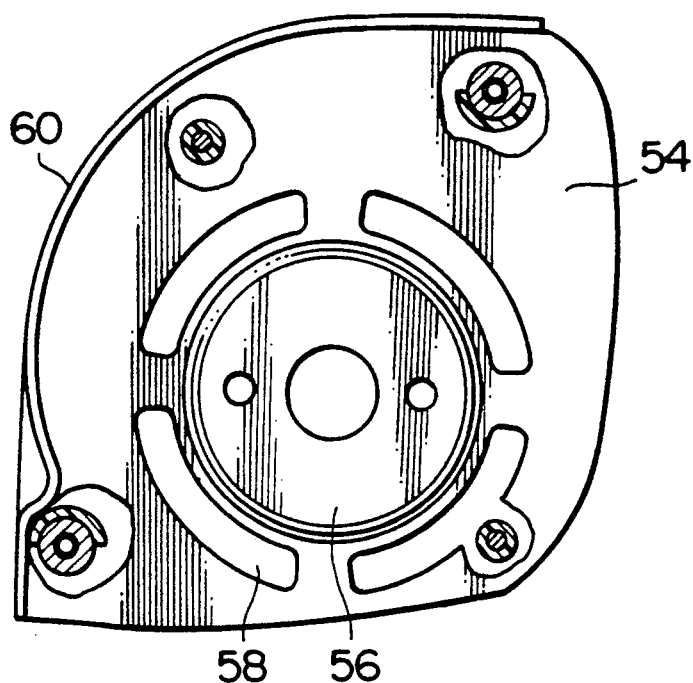
FIG. 31 is a plan view showing a mounting base plate FIG. 27.
Figure 32:
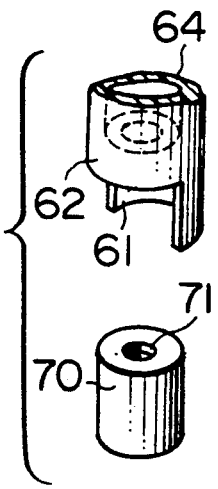
FIGS. 32 and 33 are perspective views showing the construction for mounting the mounting base plate on the casing of the receptacle, the mounting base plate being one which has been shown in FIG. 31, respectively.
Figure 33:
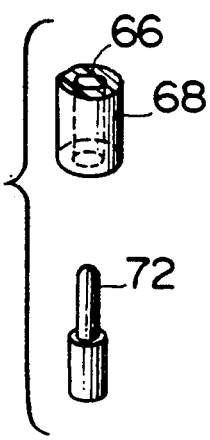

As shown in FIGS. 31 to 33, the mounting base plate 54 is integrally formed, at two positions, with mounting cylindrical protrusions 62 each having semicircular-arc like fitting portion 61 at its fore end. Each cylindrical protrusions 62 is formed, at its center, with a screw insertion bore 64 opened up to the surface of the mounting base plate 54. The semicircular-arc like sections of the fitting portions 61 of the paired cylindrical protrusions 62 are directed in opposite directions. Further, the mounting base plate 54 is integrally formed, at two positions, with a pair of cylindrical protrusions 68, respectively, which are each formed at its center with a bore 66.

On the other hand, the bottom of the receptacle 1 of the deodorizer is formed integral with cylindrical-post like protrusions 70, over which the fitting portions 61 of the cylindrical protrusions 62 of the mounting base plate 54 are fitted. The protrusion 70 is formed, at its center, with an internally threaded portion 71. Further, the bottom of the receptacle 1 is formed integral with a pin 72, which is fitted into the bore 66 of the cylindrical protrusion 68.

The fitting portion 61 of the cylindrical protrusion 62 of the mounting base plate 54 is fitted over the protrusion 70 of the receptacle 1 while the bore 66 of the cylindrical protrusion 68 is fitted onto the pin 72 of the receptacle 1. Then, a screw 74 is inserted into the bore 64 from the upper surface of the mounting base plate 54 and then is screwed into the internally threaded portion 71 of the protrusion 70. As a result, the mounting base plate 54 is fixed to the bottom of the receptacle 1.

With the above-described construction, the screw engaging portions are as smaller in number as two portions. This enables reduction in manufacturing cost and also enables the mounting base plate 54 to be positioned and fixed on the bottom of the receptacle 1. In addition, even after the fixing, it is possible to prevent the creation of backlashes due to, for example, twisting.

It is to be noted that a cavity 76 is formed between the bottom of the receptacle 1 and the bottom of the mounting base plate 54 by means of the protrusions 70 and the pins 72 (see FIG. 7).

Figure 29:
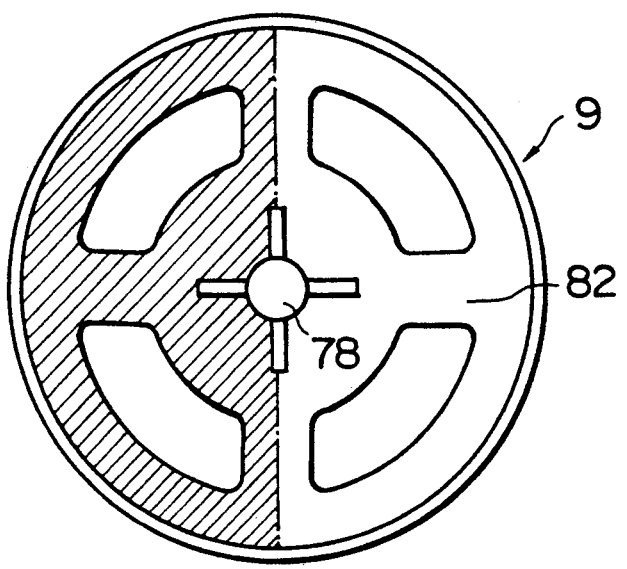
FIG. 29 is a plan view showing the fan shown in FIG. 27.
Figure 30:
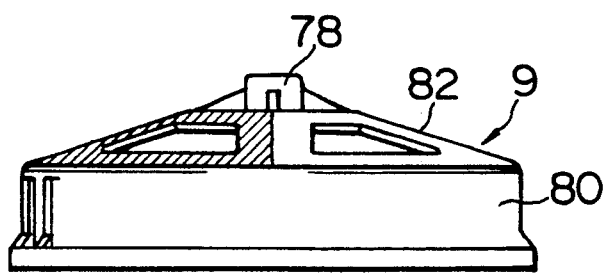
FIG. 30 is a front view of the fan of FIG. 29.

The fan 9 is made of resin. As shown in FIGS. 29 and 30, the fan 9 is constituted by a centrifugal type sirocco fan and a central portion 78 thereof is fixed to a rotational shaft (not shown) of the motor 7. The electric motor 7 is disposed inside a vane section 80 of the fan 9, for which reason, a plurality of connecting portions 82 connecting the central portion 78 of the fan 9 and the vane section 80 thereof are tapered. Since the fan 9 has its central portion allowed to project upwards, the section of the cover 3 of the receptacle 1 is shaped to have a chevron shape having gently curved slant surfaces. Further, as shown in FIGS. 29 and 30, the fan 9 has its half part so colored (hatched part) as to permit easy observation of the fan rotation through a rotary observation port as later described.

As shown in FIG. 7, the slit-shaped air suction port 17 and air blowout port 18 are provided at the opposite short-side portions of the receptacle 1 and are constructed as follows. Namely, as shown in FIG. 8, a pair of projections 84 are integrally formed on those portions of the cover 3 which are to be engaged with the casing 2. Of these projections 84, the portions corresponding to the opposite short side portions of the cover 3 are eliminated by specified lengths, respectively, whereby slit-shaped openings are formed at those eliminated portions of the projections 84 when the cover 3 are engaged with the casing 2.

Figure 12:
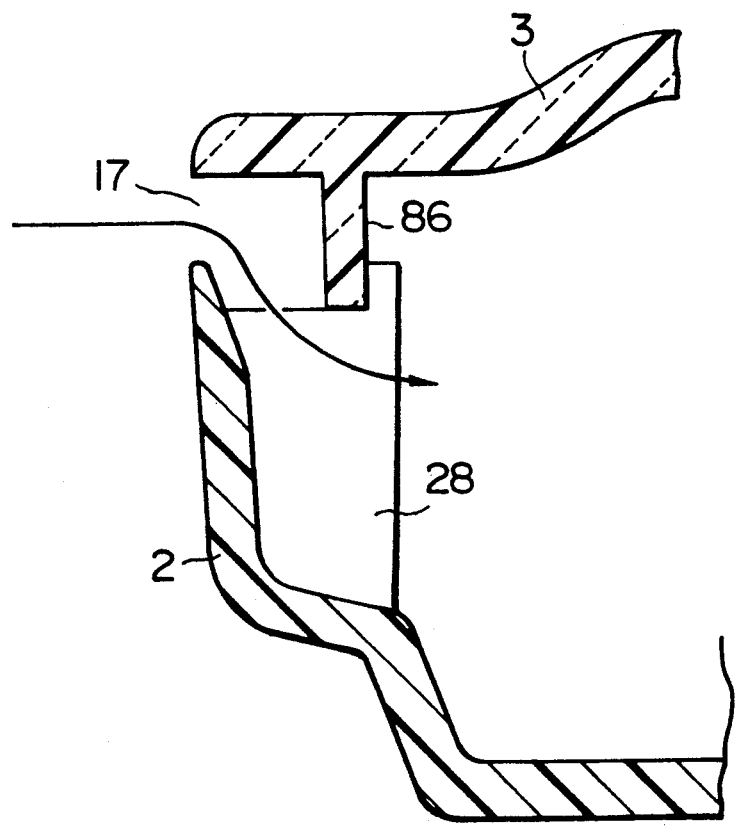
FIG. 12 is a sectional view showing, on an enlarged scale, an air suction port section shown in FIG. 7.

These slit-shaped openings are used as the air suction port 17 and the air blowout port 18, respectively. According to this construction, however, the interior of the receptacle 1 can be seen through the slit-shaped openings. According to this embodiment, therefore, another pair of projections 86 are integrally formed on the inner surface of the cover 3 in such a manner that said another pair of projections 86 are located at positions corresponding to the slit-shaped opening portions, i.e., at said eliminated portions of the projections 84 and in such a manner that said another pair of projections 86 are located inside of the projections 84. On the other hand, plate-like supporting portions for supporting the projections 86 (see FIG. 12) are integrally formed on the inner surface of the casing 2 of the receptacle 1.

With this construction, the deodorant member 5, fan 9, etc. are not seen and only the projection 86 is seen even when the interior of the rceptacle 1 is intended to be seen through the slit-shaped openings.

Figure 2:
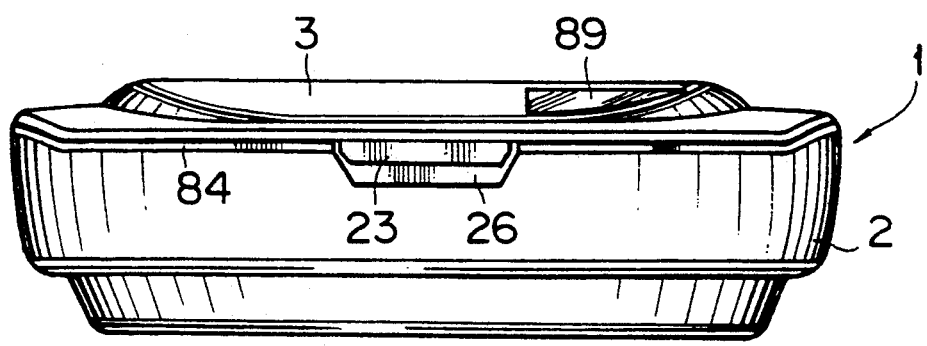
FIG. 2 is a front view of the deodorizer of FIG. 1.

At the right-hand side of the upper surface of the cover 3 of the receptacle 1 is provided the rotary observation port 89 for observing the condition of fan rotation (see FIGS. 1 and 2). This rotary observation port 89 is located so that the interior of the cover may be inspected not only from above the upper surface of the cover 3 but also from the front side and the right side of the receptacle 1, via that observation port 89. It is to be noted that the cover 3 is made of a transparent acrylic resin and is formed by an In-Mold molding technique and a specified color is printed on the same. At the time of printing, therefore, the rotaty observation port 89 can be formed by masking a portion of the cover corresponding to the port 89.

The operation of the deodorizer having the described construction will now be described.

The deodorizer is placed on, for example, a front dashboard of an automobile. When sunrays are made incident upon the solar cell 4 of the deodorizer, electrons of paired units of an electron and a positive hole produced at the pn junction portion inside the solar cell 4 due to the energy of the incident sunrays, are diffused into a n-type layer and the positive holes are diffused into a p-type layer, whereby the energy of the incident light rays are converted into electric energy. Thus, an output current is supplied to the electric motor 7 directly connected between the output electrodes of the solar cell 4. The electric motor 7 is thereby driven to rotate, so that the fan is rotated. Owing to the blowing action of the fan 9, the air in the compartment of an automobile is sucked into the receptacle 1 by way of the air suction port 17 as indicted by an arrow. When the air passes around the deodorant member 5, the air takes in deodorant components from the deodorant 32 in an amount corresponding to the degree of opening between the cap 34 of the deodorant member 5 and the container 30 thereof. Then, the air passes through the cavity 76 between the mounting base plate 54 and the bottom of the receptacle 1 and passes through the four air inlets 58 of the mounting base plate 54 and thus is sucked into the fan 9. The air thus sucked in is directed by the scroll section 60 and is blown out into the compartment of an automobile from the air blowout port 18 of the receptacle 1.

Through the above-described operation, the deodorant components which evaporates from the deodorant member 5 is mixed into the air stream and the resulting air stream is released outside the receptacle. In this way, the smell in the automobile compartment in which the deodorizer is placed is subjected to deodorization.

On the other hand, according to this embodiment, the solar cell 4 is disposed so that it may cover the deodorant member 5 and the fan 9 in the projecting direction of the slant surface thereof and so that it may overlap the imaginary plane connecting the air suction port 17 and the air blowout port 18. In consequence, the other side surface of the cover portion than that side surface, on which the solar cell 4 is mounted, faces over the blown air passage system including the air suction port 17, deodorant member 5, fan 9 and air blowout port 18.

Accordingly, since the air caused to pass through the interior of the receptacle 1 owing to the blowing action of the fan 9 flows while it is kept in contact with the other side surface of the cover portion than that side surface, on which the solar cell 4 is mounted, the flow of air continues to take away the heat inside the solar cell 4 via the cover 3 owing to heat transfer action attributable to forced convection. This enables reduction in temperature of the solar cell 4, prevention of thermal efficiency thereof and checking of decrease in service life thereof.

By the way, the deodorizer according to this embodiment and a deodorizer whose solar cell 4 is not cooled as by air stream (Comparative Example) unlike this embodiment were put on a rear tray in the compartment of an automobile parked under broiling conditions in midsummer. To compare both with each other, the deodorizer of this embodiment indicated a solar cell surface temperature of 85° C. while the comparative deodorizer indicated a solar cell surface temperature of 95° C. As seen, the deodorizer is much more excellent than that of the comparative example.

In this embodiment, a gelled deodorant is employed as the deodorant 32 of the deodorant member 5. In addition, the container 30 filled with the deodorant member 32 is formed into one having a shape shown in FIG. 14. For this reason, it is possible to maintain the deodorizing action due to the presence of the deodorant 32 for a long period of time.

Figure 22:
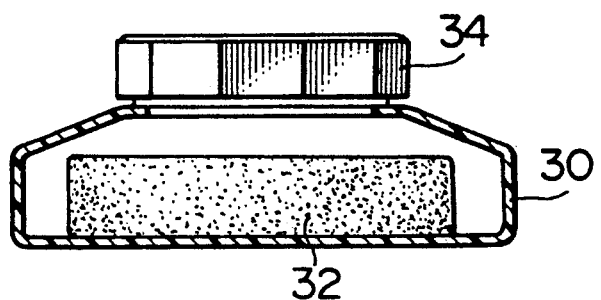
FIG. 22 is a sectional view showing a state wherein the volume of the deodorant shown in FIG. 14 is reduced.
Figure 23:
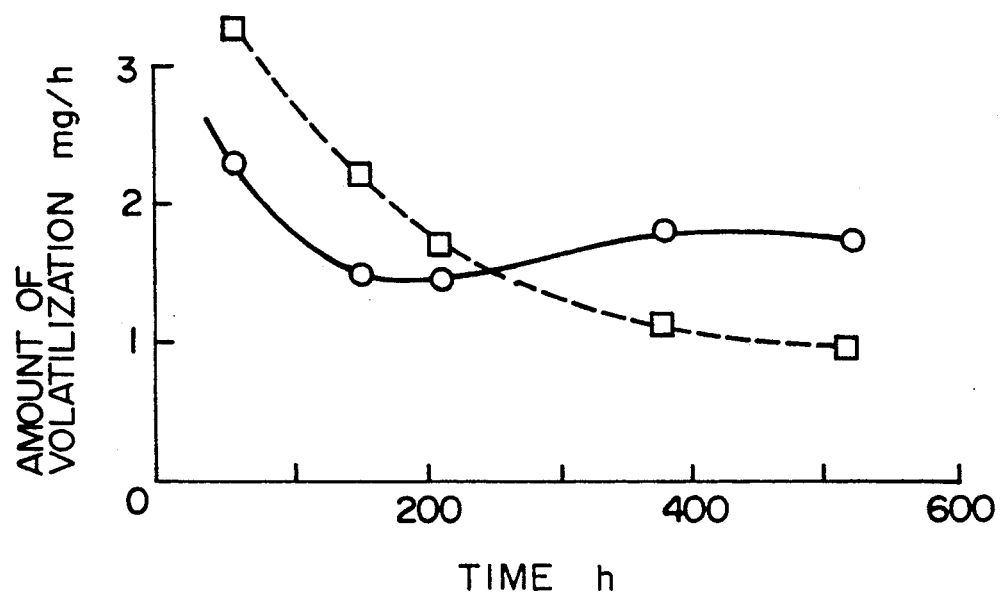
FIG. 23 graphically shows a characteristic concerning the relation of the amount of deodorant volatilized relative to the lapse of time.
Figure 24:
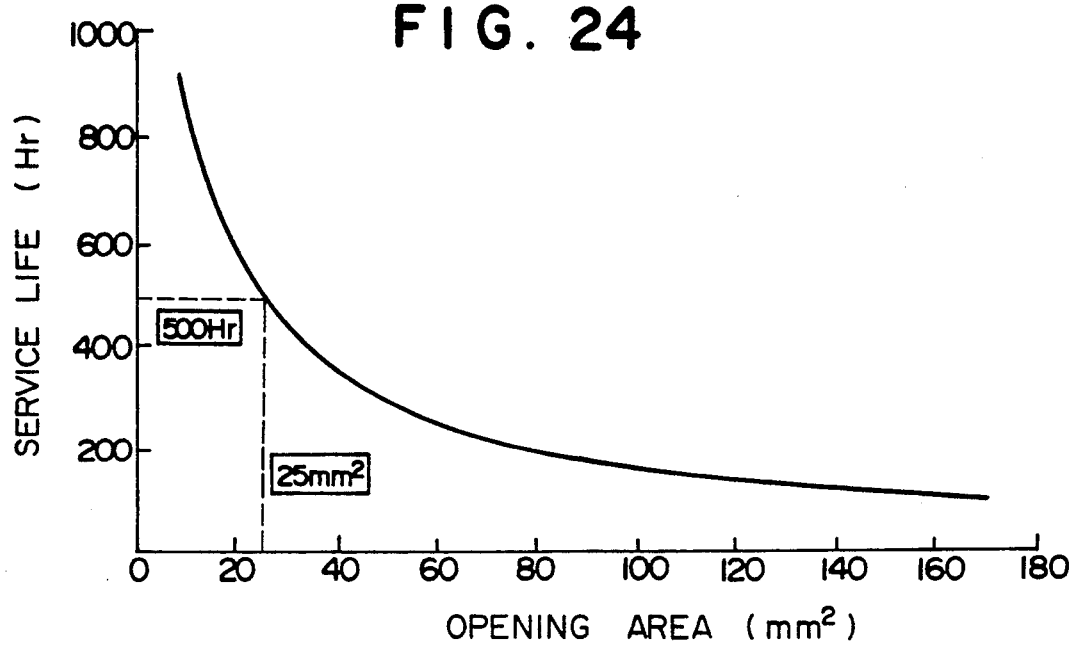
FIG. 24 graphically shows a characteristic concerning the service life of the deodorant as measured relative to the area of opening defined between the container and cap of the deodorant member shown in FIG. 13.

More specifically, at the initial stage, the deodorant 32 is filled in the deodorant member 5 up to the top surface of the container 30 thereof. Therefore, the area of evaporation and transpiration thereof is small. On the other hand, when the volume of the deodorant 32 becomes gradually smaller with the result that the upper surface of the deodorant 32 decreases from the top surface of the container 30 down to a lower surface level (corresponding to the tapered portion of the container 30), although the transpiration area of the deodorant 32 indicates no variation, the deodorant 32 shrinks as shown in FIG. 22 and as a result the transpiration area thereof substantially increases. FIG. 23 graphically shows the relationship between the amount of deodorant transpired and the lapse of time. In the Figure, a broken line indicates a case where the container is in the form of a hollow-cylindrical post while a solid line indicates a case where the container is one having a shape according to this embodiment. As will be understood from FIG. 23, the shape of the container section according to this embodiment makes it possible to suppress the initial amount of deodorant transpired and slightly increase it from a midway. Accordingly, it is seen that the deodorizing effect can be maintained for a long period of time. It is to be noted that the amount of deodorant transpired varies depending upon the extent of turning of the cap 34 relative to the container 30 of the deodorant member 5. FIG. 24 is a graph which has been prepared in this connection. Namely, in FIG. 24, the length of the service life of the deodorant 32 is plotted on the ordinate and the area of the opening defined between the cap 34 and the container 30 is plotted on the abscissa. To say an example, the desirable opening area is approximately 25 mm$^2$ if the service life extends to an extent of two to three months (about 500 hours).

This data is based on the following specification of a deodorizer in accordance with an embodiment of the present invention.

Container

Width—104 mm, Depth—140 mm, and Height—40 mm.

Air Suction Port and Air Blowout Port: Width—2.5 mm, Length—65 mm and Opening Area—162.5 mm$^2$.

Centrifugal Type Fan

Diameter—60 mm, Height—21.5 mm.

Height of Vane Section—11 mm), Number of Vanes—30.

Deodorant Member

Bottom of Container Section: Width—60 mm, Depth—40 mm, Dimension Between the Bottom and the Tapered Portion—11 mm, Height of Tapered Portion—5 mm, Radius of Arcuate of Bottom—19.7 mm, and Diameter of Cap—35 mm.

Electric System

Amorphous Silicon Type Solar Cell: Longitudinal Length—40 mm, Lateral Length—100 mm, Output Produced By Sunrays of Fine Day—0.1 Watt, Electric Motor: DC—2V, Number of Rotation—400 rpm, and Flow Rate of Air—0.2 m$^3$/h.

Meanwhile, according to this embodiment, when the cover 3 of the receptacle 1 is opened, the upper surface of the cover 3 on which the solar cell 4 is installed is allowed to face downwards. In consequence, the solar cell 4 ceases to receive the sunrays, so that the rotation of the fan 9 is stopped. For this reason, at the time of replacing the deodorant member 5, opening the cover 3 permits rotation of the fan 9 to be automatically stopped. This makes it possible to replace the deodorant member 5 with high level of safety. In addition, since no use is made of any switch or the like, the construction of the deodorizer is simplified.

Further, in this embodiment, the rotary observation port 89 is formed at the right end portion of the cover 3 of the receptacle 1 so as to permit seeing the inside of the cover 3 from above the upper surface of the cover 3, the front side of the receptacle and the right side thereof. In addition, in an automobile with a handle at the right side thereof in particular, the deodorizer is installed at the left-hand side of the front dashboard. For the reasons mentioned above, the condition of rotation of the fan 9 can be easily observed through the rotary observation port 89 without largely deviating the driver's face posture from the forwardly directed driver's face direction, thus contributing to safety driving of the automobile.

In this embodiments the air suction port 17 and the air blowout port 18 are formed between the respective joining surfaces of the casing 2 and cover 3 of the receptacle 1. For example, therefore, design of the deodorizer looks clean as compared with the case where the ports 17 and/or the port 18 are formed in the casing 2 or cover 3. In addition, since the ports 17, 18 are formed with the projections 86, respectively, the deodorant member 5, fan, etc. inside the receptacle 1 can not be seen through the ports 17, 18 as the projections 86 is in the way.

According to this embodiment, the upper portion of the fan 9 is shaped to have a convex shape and, in addition, the electric motor 7 is disposed inside the fan 9, thereby making small the height of the motor 7 and the fan 9. In addition, the cover 3 of the receptacle 1 is shaped to have a chevron shape in section whose top is located in the vicinity of a center axis of the fan 9 and which has gently curved slant surfaces.

With the construction, the upper convexed portion of the fan 9 can be readily accommodated within the receptacle 1. In addition, the solar cell 4 is provided on the inclined surface of the chevron-shaped cover 3. This can make it easy for the sunrays to be irradiated onto the solar cell 4.

Further, according to this embodiment, the blown air passage system of the deodorizer is arranged such that the air suction port 17, deodorant member 5, fan 9 and air blowout port 18 are disposed substantially in straight line. Consequently, the deodorizer per se can be made flat with the result that, even if the deodorizer is installed on the front dashboard or rear tray, it will not become an obstacle to forward or rearward visibility. Besides, the pressure loss of the blown air passage system can be suppressed to a minimum value. Consequently, the output of the electric motor 7 can be made small. In consequence, it is possible to make the solar cell 4 small in size.

According to this embodiment, the solar cell 4 is adhered in the depression 14 of the slant surface 12 of the outer cover 3 surface with the so-called duplicated tape 16 interposed therebetween, the tape 16 having the elastic base plate provided, on both surfaces thereof, with adhesive layers respectively. Therefore, the thermal stress acting on the glass substrate of the solar cell 9 can be absorbed by the elastic base plate of the duplicated tape 16 owing to the difference in coefficient of thermal expansion between the glass substrate of the solar cell 4 and the cover of the receptacle 1. Further, the mechanical stress produced due to the vibrations of the deodorizer per se, can also be absorbed by the elastic base plate of the duplicated tape 16.

According to this embodiment, the cap 34 is so arranged as to be stopped at its predetermined position relative to the container 30 of the deodorant member 5. Therefore, it is possible to prevent the cap 34 from being excessively opened due to, for example, the vibrations of an automobile involved. Besides, it is also possible to prevent a child from erroneously putting the deodorant 32 into his mouth.

Figure 35:
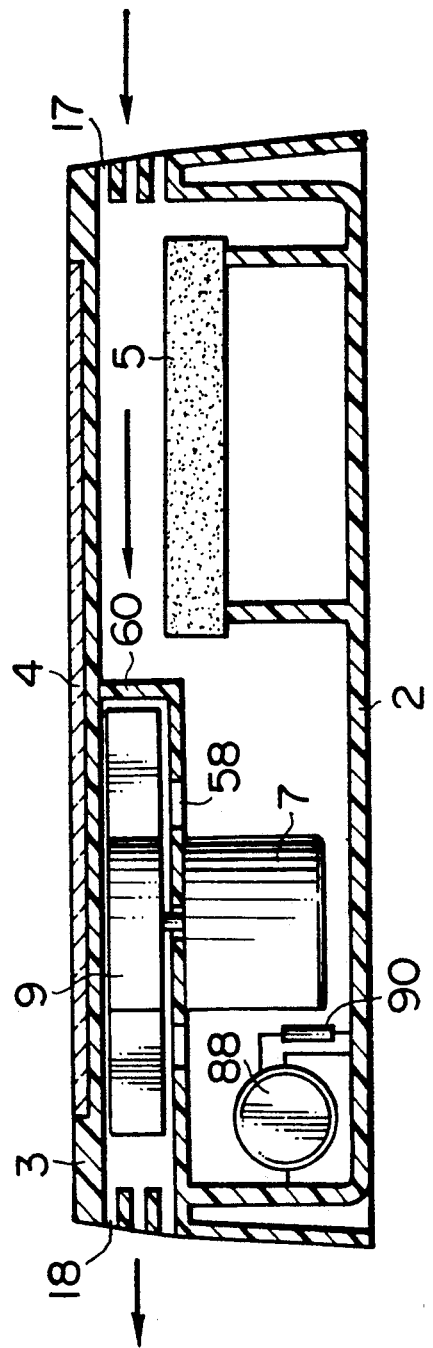
FIG. 35 is a deodorizer in accordance with another embodiment of the present invention, illustrating a sectional view taken along the line XXXV—XXXV of FIG. 36.
Figure 36:
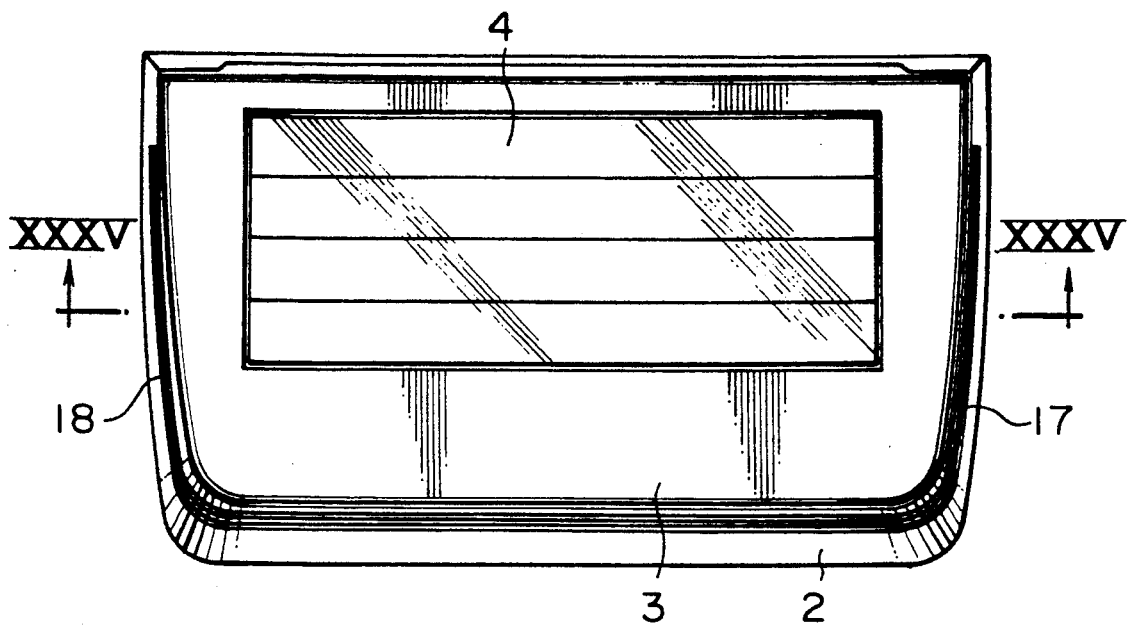
FIG. 36 is a plan view of the deodorizer in accordance with the second embodiment of the present invention.
Figure 37:
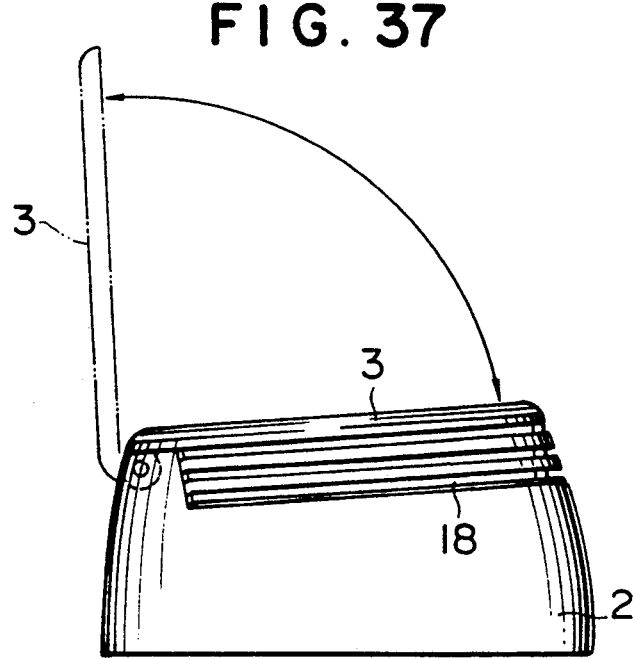
FIG. 37 is a side view of the deodorizer of FIG. 36.

FIGS. 35 to 37 shows a deodorizer in accordance with another embodiment of the present invention, in which the same or equivalent parts or sections as those in the preceding embodiment are denoted by like reference numerals, respectively, and description of the construction thereof is omitted. In this second embodiment, a compact-sized battery 88 such as a nickel-cadmium battery, which is electrically charged by the generated output of the solar cell 4, is installed inside the casing 2. Namely, the battery 88 is so arranged as to be electrically chaged by excessive generated output of the solar cell 4. Accordingly, when no incident light ray energy is obtained from the sunrays as at night, the battery 88 is used to cause the electric motor 7 to be driven for rotation, thereby enabling the use of the deodorizer. Numeral 90 denotes an anti-reverse-current diode which is inserted and connected between one output end of the solar cell 4 and one end of the battery 88. A Schottky barrier diode whose forward voltage drop is small (approximately 0.3 V) is employed as such anti-reverse-current diode. As shown in FIG. 35 by arrows, air flow entering into the receptacle from the air suction port 17 passes through the interior of the receptacle while contacting with the rear surface of the cover 3 to cool the solar cell 4.

Figure 38:
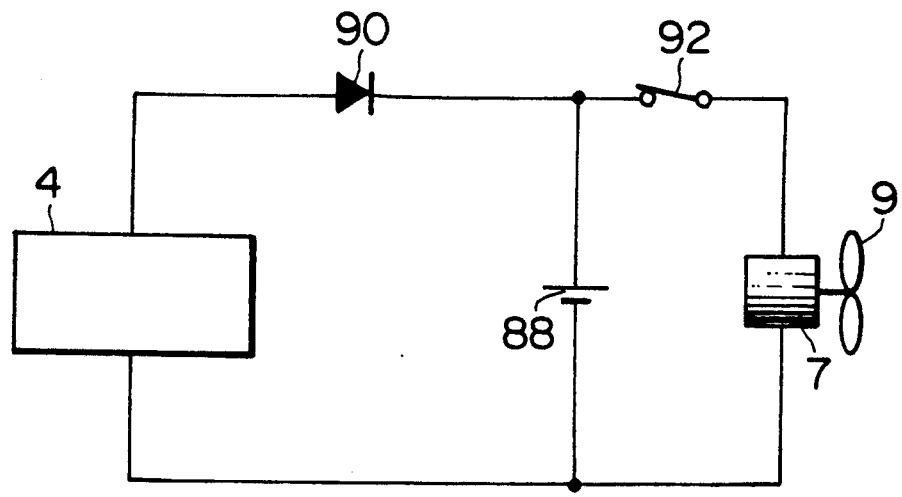
FIG. 38 is an electric circuit diagram showing a solar cell and an electric motor employed in the deodorizer in accordance with the second embodiment of the present invention.

An electric circuit diagram of this embodiment is shown in FIG. 38, in which numeral 92 is a switch. According to this embodiment, the connection between the solar cell 4 and the electric motor 7 is made "ON" or "OFF" by operation of the switch 92.

Figure 39:
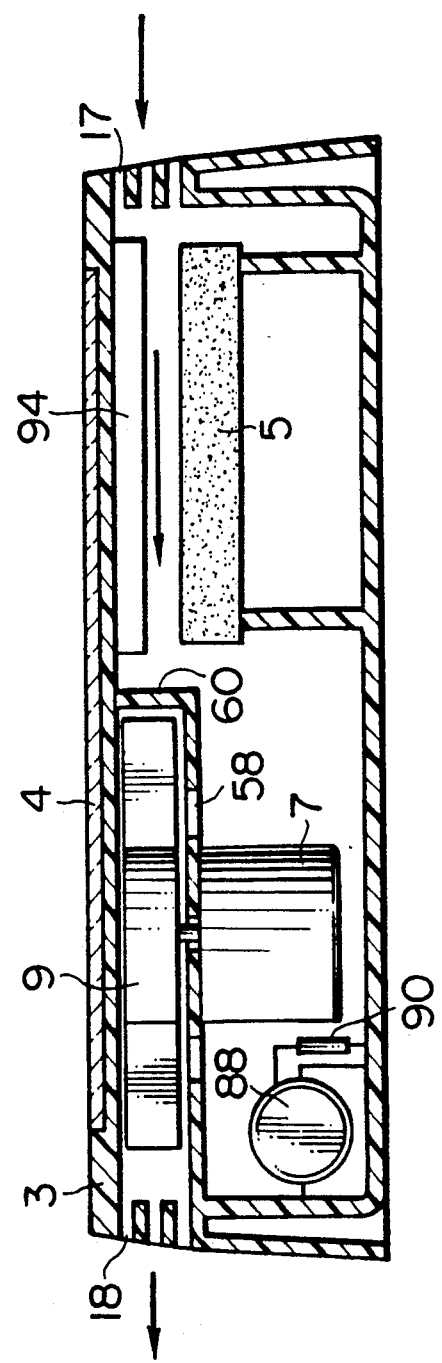
FIG. 39 shows a deodorizer in accordance with still another embodiment of the present invention.

FIG. 39 shows a deodorizer in accordance with still another embodiment of the present invention, in which the same or equivalent parts or sections as those in the preceding embodiments are denoted by like reference numerals and description of the construction thereof is omitted. In the third embodiment, the other side surface of the cover 3 portion than that side surface, on which the solar cell 4 is installed, is formed with a plurality of cooling fins 94, thereby enhancing the effect of cooling the solar cell 4. It is to be noted that the cooling fins 94 may be formed integral with the cover 3 but that the cooling fins 94 which have been prepared separately may be joined to the cover 3.

Figure 40:
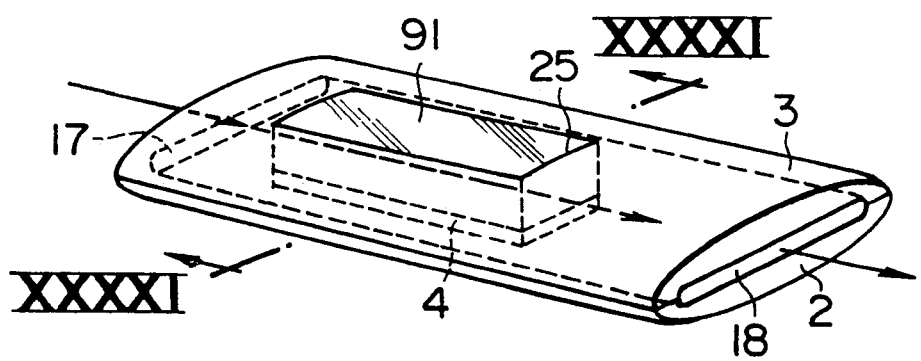
FIG. 40 is a perspective view of a deodorizer in accordance with a further, or a fourth, embodiment of the present invention.
Figure 41:
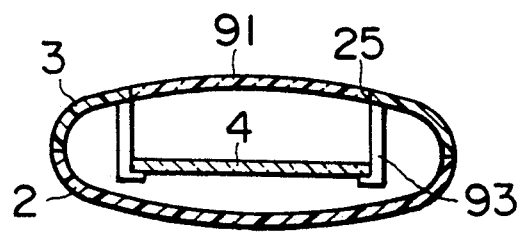
FIG. 41 is a sectional view taken along the line XXXXI—XXXXI of FIG. 40.

FIGS. 40 and 41 show a deodorizer in accordance with a further embodiment of the present invention. According to this embodiment, the solar cell 4 is installed within the receptacle 1. More specifically, an opening 25 is provided in the cover 3 and a plate 91 made of transparent resin such as acrylic resin is fixed to the cover 3 in such a manner as to cover the opening 25. Thereafter, the solar cell 4 is suspended within the casing 2 toward the bottom thereof by means of suspension members 93. Incidentally, the other constructions are the same as those stated in connection with FIGS. 1 to 34 and therefore description thereof is omitted.

With this construction, the sunrays reach the solar cell 4 within the casing 2 through the transparent-resin plate 91 and the opening 25. Further, the air which flows through the interior of the receptacle 1 is allowed to flow while it is kept in contact with the upper and lower surfaces of the solar cell 4, therby enhancing the effect of cooling the solar cell 4. Arrows in the Figure indicate the flow of the air.

The present invention is not limited to the above-described embodiments but permits various modifications and changes to be made as follows.

(1) The deodorant of the deodorant member 5 may be not aromatic, and may be not in the form of gel but in the form of liquid. Further, deodorant may be a substance such as activated carbon.

(2) The air suction port and air blowout port are not limited to the slit-shaped ones. For example, a plurality of bores may be formed in the upper surface of the cover and used as such ports.

(3) The construction wherein the cover is openably attached to the casing of the receptacle can be variously conceivable. For example, the cover may be completely separable from the casing.

(4) The dimensions of the constituent members or sections which have been described above are only one example. Needless to say, various changes or alterations may be course be possible.

What is claimed is:

1. A deodorizer for a motor vehicle, said deodorizer comprising:
   receptacle means including an opening and a cover for covering said opening, said receptacle means being being shaped to have one end side and an other end side;
   a deodorant member disposed within said receptacle means;
   an electric motor disposed within said receptacle means, and a fan driven by said electric motor;
   said receptacle means being formed with an air suction port provided on the one end side of said receptacle means and an air blowout port provided on the other end side of said receptacle means in a way such that a plane connects said air suction port and air blowout port; and
   a solar cell provided on a mounting surface of said cover corresponding to an area between said air suction port and said air blowout port and connected to supply a driving power to said electric motor; a part of said fan being within said plane, and said mounting surface located facing said plane such that a blowing action provided by the rotation of said fan from said electric motor causes airflow passing through the interior of said receptacle means to pass over a rear portion of said mounting surface of said cover to thereby cool said solar cell; wherein
   said receptacle means further includes means for controlling the rotation of said fan and said electric motor comprising means for mounting said solar cell obliquely to rays from a source of light energy when said cover is in an open position to prevent rotation of said fan and for presenting said solar cell substantially perpendicularly to said rays when said cover is in a closed position to induce rotation of said fan; and
   said receptacle means has a substantially flat vertical cross-section and is further constructed so as to present a restricted passageway to increase the velocity of air flowing therethrough.

2. A deodorizer comprising:
   receptacle means including a casing having a flat opening at its top and a concave-shaped cross-section and a cover shaped to cover said opening and provided on said casing in a manner to make said opening openable and closable, said casing being rectangular in shape and shaped to have one end and an other end opposite to said one end with said opening interposed therebetween and formed with an air suction port provided at the one end of said receptacle means and an air blowout port provided at the other end of said receptacle means;
   an electric motor disposed within said receptacle means to oppose said air blowout port with a centrifugal fan fixed to said electric motor, an intake side of said fan facing said air suction port and an outlet side of said fan facing said air blowout port;
   a deodorant member disposed between said air suction port and said air blowout port within said receptacle means; and
   a solar cell provided on an outer surface of said cover for supplying a driving power to said electric motor; said air suction port and said air blowout port being disposed in substantially a same horizontal plane;
   said cover having a rear surface, opposite to said outer surface, and disposed adjacent to said horizontal plane when said cover covers said opening of said casing, whereby a blowing action of said fan causes airflow passing from said air suction port through the interior of said receptacle means and discharging from said air blowout port to flow in contact with said rear surface of said cover of said receptacle means to thereby cool said solar cell through said rear surface of said cover; wherein
   said receptacle means further includes means for controlling the rotation of said fan and said electric motor comprising means for mounting said solar cell obliquely to rays from a source of light energy when said cover is in an open position to prevent rotation of said fan and for presenting said solar cell substantially perpendicularly to said rays when said cover is in a closed position to induce rotation of said fan; and
   said receptacle means has a substantially flat vertical cross-section and is further constructed so as to present a restricted passageway to increase the velocity of air flowing therethrough.

3. A deodorizer comprising:
   receptacle means including an opening and a cover for covering said opening, said receptacle means being shaped to have one end side and an other end side opposite to said one end side, said receptacle means having an air suction port provided on the one end side of said receptacle means and an air blowout port provided on the other end side of said receptacle means in a way such that a plane connects said air suction port and said air blowout port;
   a deodorant member disposed within said receptacle means;
   an electric motor disposed within said receptacle means and a fan fixed to said electric motor to blow air from said air suction port to said air blowout port, at least a part of said fan being in said plane; and a solar cell shaped to have one end side and an other end side opposite to the one end side and connected to supply a driving power to said electric motor, said solar cell being mounted in a mounting area of an outer surface of said receptacle means between said air suction port and said air blowout port such that said one end side of said solar cell is adjacent to said air suction port and said other end side of said solar cell is adjacent to said air blowout port, a rear of said mounting area being close to and facing said plane whereby a blowing action of said fan causes airflow passing through the interior of said receptacle means from said air suction port and discharging from said air blowout port to flow in contact with said rear of said mounting area so that said solar cell is cooled by airflow over said mounting area; wherein said receptacle means further includes means for controlling the rotation of said fan and said electric motor comprising means for mounting said solar cell obliquely to rays from a source of light energy when said cover is in an open position to prevent rotation of said fan and for presenting said solar cell substantially perpendicularly to said rays when said cover is in a closed position to induce rotation of said fan; and said receptacle means has a substantially flat vertical cross-section and is further constructed so as to present a restricted passageway to increase the velocity of air flowing therethrough.

4. A deodorizer according to claim 2, wherein said air suction port and said air blowout port are formed between respective joining surfaces of said casing and said cover.

5. A deodorizer according to claim 2, wherein a substrate of said solar cell is glass, a depression is formed on said outer surface of said cover, to which depression an elastic body is adhered, said elastic body accommodating a difference in coefficient of thermal expansion between said glass substrate of said solar cell and said cover, and wherein said solar cell is disposed on said elastic body.

6. A deodorizer according to any one of claims 1 to 3, wherein said receptacle means is substantially square in cross section and is substantially flat in vertical section.

7. A deodorizer according to claim 1 or 3, wherein said fan is a centrifugal fan.

8. A deodorizer according to any one of claims 1 to 3, wherein said surface on which said solar cell is installed is in the form of an inclined surface.

9. A deodorizer according to any one of claims 1 to 3, wherein said electric motor is directly driven to rotate by the action of said solar cell.

10. A deodorizer according to any one of claims 1 to 3 wherein said cover is formed with a rotary observation port through which said fan can be observed.

11. A deodorizer according to claim 10, wherein said fan includes a colored portion on a surface of said fan and is positioned so as to be visually inspected through said rotary observation port, said colored portion enabling a visual determination of rotation and stoppage of said fan.

12. A deodorizer according to any one of claims 1 to 3, wherein said deodorant member includes a container section, a transpiration type deodorant accommodated within said container section, and a cap rotatably mounted over said container section.

13. A deodorizer according to claim 12, wherein said container section of said deodorant member is detachably mounted within said receptacle means.

14. A deodorizer according to claim 12, wherein said container section comprises a cylindrical portion having a uniform cross-sectional area for mounting thereon said cap, a tapered portion, of which a cross-sectional area gradually increases downward from said cylindrical portion, and an enlarged cylindrical portion extending from the end of said tapered portion and having a uniform cross-sectional area.

15. A deodorizer according to claim 14, wherein said cylindrical portion of said container section includes detent means for preventing disengagement of said cap.

16. A deodorizer for a motor vehicle, said deodorizer comprising:
a receptacle including a casing having a flat opening at its top and a concave-shaped cross-section and a cover shaped to cover said opening and provided on said casing in a manner to make said opening openable and closable, said casing being rectangular in shape and shaped to have one end and an other end opposite to said one end with said opening interposed therebetween and formed with an air suction port provided at the one end of said receptacle and an air blowout port provided at the other end of said receptacle;
an electric motor disposed within said receptacle to oppose said air blowout port with a centrifugal fan fixed to said electric motor, an intake side of said fan facing said air suction port and an outlet side of said fan facing said air blowout port;
a deodorant member disposed between said air suction port and said air blowout port within said receptacle; and
a solar cell provided on an outer surface of said cover for supplying a driving power to said electric motor; said air suction port and aid air blowout port being disposed in substantially a same horizontal plane;
said cover having a rear surface, opposite to said outer surface, and disposed adjacent to said horizontal plane when said cover covers said opening of said casing, whereby a blowing action of said fan causes airflow passing from said air suction port through the interior of said receptacle and discharging from said air blowout port to flow in contact with said rear surface of said cover of said receptacle to thereby cool said solar cell through said rear surface of said cover;
projections, formed on rectangular side surfaces of said cover adjacent to said air suction port and said air blowout port within said receptacle, and
means within said receptacle for holding tip ends of said projections,
said projections located such that when said opening of said receptacle is closed, surfaces of said projections form offset passages which prevent the interior of said casing from being directly and visually inspected through said air suction port and said air blowout port.

17. A deodorizer comprising:
receptacle means including a casing having an opening at its top and a concave-shaped cross-section and shaped to have one end side and an other end side opposed to said one end side;
a cover shaped to cover said opening and provided on said casing in a manner to make said opening openable and closable and having a mating face between said cover and said casing when said opening is closed;

a deodorant member disposed within said casing;

an electric motor disposed within said receptacle means having a fan fixed to said electric motor;

an air suction port and an air blowout port provided on said mating face of said casing and said cover when said opening of said casing is closed by said cover, said air suction port and air blowout port being in a same plane; and a solar cell for supplying a driving power to said electric motor;

said air suction port being disposed on said one end side of said casing and said air blowout port being disposed on the other end side of said casing, said cover being substantially flat at an outer surface of a portion corresponding to an area between said air suction port and said air blowout port, said solar cell being disposed on the substantially flat outer surface of said cover, and said casing formed such that said flat portion is close to and faces said plane and such that a blowing action of said fan causes airflow passing through the interior of said receptacle means to flow in contact with a rear side surface of said substantially flat outer surface, so that said solar cell is cooled through said rear side surface of said substantially flat outer surface; wherein said receptacle means further includes means for controlling the rotation of said fan and said electric motor comprising means for mounting said solar cell obliquely to rays from a source of light energy when said cover is in an open position to prevent rotation of said fan and for presenting said solar cell substantially perpendicularly to said rays when said cover is in a closed position to induce rotation of said fan; and said receptacle means has a substantially flat vertical cross-section and is further constructed so as to present a restricted passageway to increase the velocity of air flowing therethrough.

18. A deodorizer for comprising:

receptacle means including a casing having an opening at its top and a concave-shaped cross-section and a cover having an outer surface and a rear surface, opposite to said outer surface, and shaped to cover said opening and provided on said casing in a manner to make said opening openable and closable, said casing being shaped to have one end and an other end with said opening interposed therebetween and formed with an air suction port provided at the one end and an air blowout port provided at the other end, said air suction port and air blowout port being disposed in substantially the same horizontal plane;

an electric motor comprising a centrifugal fan disposed between said air suction port and air blowout port in a manner to be close to and face the rear surface side of said cover, said fan being fixed to said electric motor to be rotated thereby;

a deodorant receptacle disposed between said air suction port and said electric motor within said receptacle means and accommodating therein a deodorant member; and a solar cell provided on a portion of an outer surface of said cover which portion corresponds to an area between said air suction port and said air blowout port, said solar cell supplying a driving power to said electric motor whereby airflow is produced to pass through the interior of said receptacle means from said air suction port to said air blowout port; and wherein a blowing action produced by rotation of said centrifugal fan causes airflow entering from said air suction port into the interior of said receptacle means and sucked into said centrifugal fan to come close to and pass over said rear surface side of said cover so that said solar cell is cooled by airflow over said rear surface side of said cover; wherein said receptacle means further includes means for controlling the rotation of said fan and said electric motor comprising means for mounting said solar cell obliquely to rays from a source of light energy when said cover is in an open position to prevent rotation of said fan and for presenting said solar cell substantially perpendicularly to said rays when said cover is in a closed position to induce rotation of said fan; and said receptacle means has a substantially flat vertical cross-section and is further constructed so as to present a restricted passageway to increase the velocity of air flowing therethrough.

19. A deodorizer according to claim 18, wherein said cover has a front face side and a rear face side, and a transparent, rotary observation port is formed on said outer surface adjacent to said front face side, which port serves for observation of a rotation condition of said fan.

* * * * *